(12) United States Patent
Cheng et al.

(10) Patent No.: US 11,177,024 B2
(45) Date of Patent: Nov. 16, 2021

(54) IDENTIFYING AND INDEXING DISCRIMINATIVE FEATURES FOR DISEASE PROGRESSION IN OBSERVATIONAL DATA

(71) Applicant: International Business Machines Corporation, Armonk, NY (US)

(72) Inventors: Yu Cheng, Ossining, NY (US); Soumya Ghosh, Boston, MA (US); Jianying Hu, Bronx, NY (US); Ying Li, Fort Lee, NJ (US); Zhaonan Sun, Elmsford, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 622 days.

(21) Appl. No.: 15/799,664

(22) Filed: Oct. 31, 2017

(65) Prior Publication Data
US 2019/0130070 A1 May 2, 2019

(51) Int. Cl.
*G16H 10/60* (2018.01)
*G16H 50/50* (2018.01)
*G06Q 10/10* (2012.01)

(52) U.S. Cl.
CPC .............. *G16H 10/60* (2018.01); *G16H 50/50* (2018.01); *G06Q 10/10* (2013.01)

(58) Field of Classification Search
CPC combination set(s) only.
See application file for complete search history.

(56) References Cited

U.S. PATENT DOCUMENTS 9,589,104 B2 * 3/2017 Heywood et al.
2004/0172225 A1 * 9/2004 Hochberg et al.
2004/0243362 A1 * 12/2004 Liebman
(Continued)

FOREIGN PATENT DOCUMENTS

EP 917078 A1 5/1999

OTHER PUBLICATIONS

Cook et al., "Disease Progression Modeling—Key Concepts and Recent Developments," Pharmacometrics, Apr. 15, 2016, pp. 221-230, Springer International Publishing AG, 10 pages.
(Continued)

*Primary Examiner* — Michael Tomaszewski
*Assistant Examiner* — William T. Monticello
(74) *Attorney, Agent, or Firm* — Amin, Turocy & Watson, LLP

(57) ABSTRACT

A system (or method) for generation and employment of disease progression model(s) that facilitates identifying and indexing discriminative features for disease progression in observational data. The disease progression prediction system comprises a processor that executes computer executable components stored in memory. A receiving component receives and learns observational patient data. A model generation component builds a preliminary disease progression model. An identification component identifies discriminative clinical features for different disease stages. A ranking component ranks discriminative powers of clinical features for respective pairs of disease stages; wherein the model generation component employs the ranked features to generate a final disease progression model.

18 Claims, 11 Drawing Sheets

(56) References Cited

U.S. PATENT DOCUMENTS

| | | | |
|---|---|---|---|
| 2009/0106004 A1* | 4/2009 | Edwards et al. | |
| 2010/0088264 A1* | 4/2010 | Teverovskiy et al. | |
| 2012/0004893 A1 | 1/2012 | Vaidyanathan et al. | |
| 2014/0297241 A1 | 10/2014 | Barhak | |
| 2016/0026917 A1* | 1/2016 | Weisberg et al. | |
| 2016/0232324 A1* | 8/2016 | Liu et al. | |
| 2016/0300036 A1 | 10/2016 | Ramazzotti et al. | |
| 2017/0103174 A1 | 4/2017 | Kim et al. | |
| 2017/0140109 A1 | 5/2017 | Kheifetz et al. | |
| 2017/0228507 A1* | 8/2017 | Bottinger et al. | |
| 2017/0242979 A1* | 8/2017 | Holohan | |
| 2018/0315182 A1* | 11/2018 | Rapaka et al. | |
| 2019/0027252 A1* | 1/2019 | Calhoun et al. | |
| 2019/0148019 A1* | 5/2019 | Bundschus et al. | |

OTHER PUBLICATIONS

Shiga et al., "Two-step feature selection for predicting survival time of patients with metastatic castrate resistant prostate cancer," F1000Research, Nov. 16, 2016, version 1, 10 pages.

Kong et al., "Discriminative Feature Selection for Uncertain Graph Classification," Cornell University Library, Jan. 28, 2013, arXiv.org > cs > arXiv:1301.6626v1, 12 pages.

Nilashi et al., "Accuracy Improvement for Predicting Parkinson's Disease Progression," Scientific Reports 6, Article No. 34181, Sep. 30, 2016, 18 pages.

\* cited by examiner

US 11,177,024 B2

IDENTIFYING AND INDEXING DISCRIMINATIVE FEATURES FOR DISEASE PROGRESSION IN OBSERVATIONAL DATA

TECHNICAL FIELD

The subject disclosure relates generally to observational databases such as registry data and electronic health records (EHR) that contain longitudinal information about patients, which are instrumental in tracking progression of chronic disease.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, computer-implemented methods, apparatus and/or computer program products that facilitate determining privacy for a user and a product in a particular context are described.

One or more embodiments provides for generation and employment of disease progression model(s) that facilitate identifying and indexing discriminative features for disease progression in observational data. Tracking disease progression directly based on 'raw' observational datasets can be difficult. First, multiple clinical assessments can collect observational data for various purposes, and tracking disease progression may not be a primary goal when observational data is collected. Therefore, not all assessments may be relevant for purpose of tracking disease progression. Second, among a set of assessments targeting for monitoring disease progression, there can be variance across assessments with respect to sensitivity and efficiency in discriminating patients at different disease stages. An assessment may not have the same discriminative power across a whole course of a target disease. Third, disease stages may not have clear and well accepted definition, especially for complex diseases and rare diseases, which makes the problem more complicated. Embodiments provide for identifying discriminative clinical features for tracking disease progression, and evaluating discriminative powers of clinical features at different stages of a target disease.

According to an embodiment, a disease progression prediction system is provided. The system, comprises a processor that executes computer executable components stored in memory. A receiving component receives and learns observational patient data. A model generation component builds a preliminary disease progression model. An identification component identifies discriminative clinical features for different disease stages. A ranking component ranks discriminative powers of clinical features for respective pairs of disease stages; wherein the model generation component employs the ranked features to generate a final disease progression model.

In another embodiment, a method for generating a machine-learning disease progression model comprises using a processor to execute computer executable instructions to perform the following acts: receiving and learning observational patient data, and building a preliminary disease progression model; identifying discriminative clinical features for different disease stages; and ranking discriminative powers of clinical features for respective pairs of disease stages to generate a final disease progression model.

In yet another embodiment, a computer program product for monitoring disease progression is provided. The computer program product comprises a computer readable storage medium having program instructions embodied therewith, the program instructions are executable by a processor to cause the processor to: receive and learn observational patient data, and build a preliminary disease progression model; identify discriminative clinical features for different disease stages; and rank discriminative powers of clinical features for respective pairs of disease stages to generate a final disease progression model.

DETAILED DESCRIPTION

Figure 1:
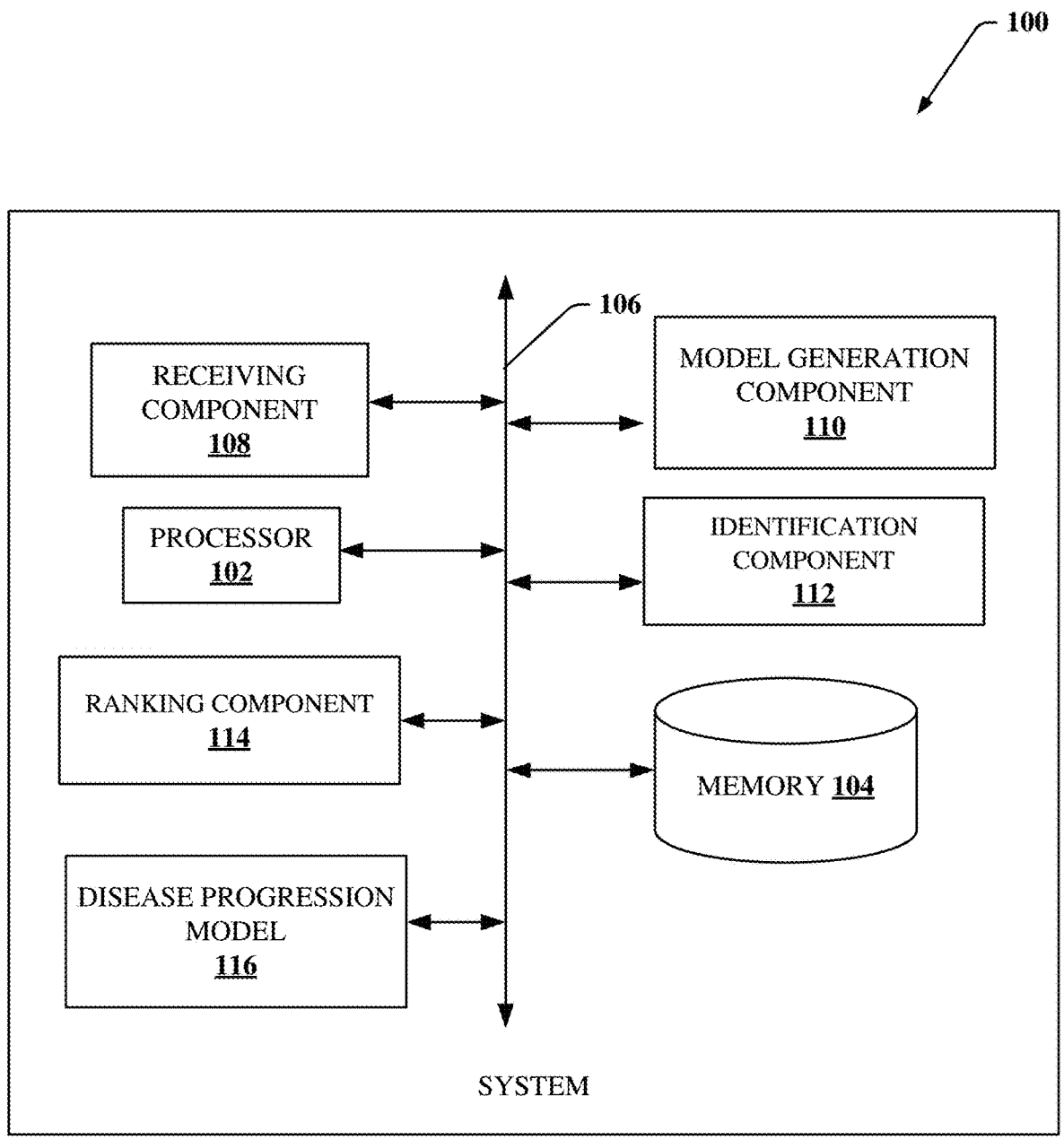
FIG. 1 illustrates a block diagram of an example system that provides for generation and employment of disease progression model(s) that facilitate identifying and indexing discriminative features for disease progression in observational data in accordance with one or more implementations described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident; however, in various cases, that the one or more embodiments can be practiced without these specific details.

One or more embodiments provides for generation and employment of disease progression model(s) that facilitate identifying and indexing discriminative features for disease progression in observational data. Tracking disease progression directly based on 'raw' observational datasets can be difficult. First, multiple clinical assessments can collect observational data for various purposes, and tracking disease progression may not be a primary goal when observational data is collected. Therefore, not all assessments may be relevant for purpose of tracking disease progression. Second, among a set of assessments targeting for monitoring disease progression, there can be variance across assessments with respect to sensitivity and efficiency in discriminating patients at different disease stages. An assessment may not have the same discriminative power across a whole course of a target disease. For example, chorea symptom is most prominent in early to middle stages of Huntington's Disease (HD). An assessment for measuring the chorea symptom may not be as efficient for late stage HD patients. Third, disease stages may not have clear and well accepted definition, especially for complex diseases and rare diseases, which makes the problem more complicated. Embodiments provide for identifying discriminative clinical features for tracking disease progression, and evaluating discriminative powers of clinical features at different stages of a target disease.

In the current state of art, clinical features are often selected for tracking progression of a target disease based on: observations and experiences of domain experts; and existing reliability & efficiency as reported in medical literature. While some well understood diseases may have well accepted staging definition, for most conditions, such staging system does not exist. Absent in the state of the art, the subject innovation provides for systematically and objectively identifying clinical features that have discriminative power to distinguish patients at different disease stage, based on observational data.

One or more embodiments of the subject disclosure is directed to computer processing systems, computer-implemented methods, apparatus and/or computer program products that facilitate efficiently, effectively, and automatically (e.g., without direct human involvement), systematically and objectively identify clinical features that have discriminative power to distinguish patients at different disease stage, based on observational data in a particular context. The computer processing systems, computer-implemented methods, apparatus and/or computer program products can employ hardware and/or software to solve problems that are highly technical in nature (e.g., adapted to perform automated determination of a ranking score for patients at different disease stage in a particular context, adapted to generate and/or employ one or more different detailed, specific and highly-complex models) that are not abstract and that cannot be performed as a set of mental acts by a human. For example, a human, or even thousands of humans, cannot efficiently, accurately and effectively manually gather and analyze thousands of data elements from observational data related to, for example, patient features, clinical features, diagnostic features, prognostic features, disease stage features and/or user feedback in a real-time network based computing environment to objectively identify clinical features that have discriminative power to distinguish patients at different disease stage, based on the observational data.

FIG. 1 illustrates a block diagram of an example, non-limiting system 100 that facilitates identifying discriminative clinical features for tracking disease progression, and evaluating discriminative powers of clinical features at different stages of a target disease in a particular context in accordance with one or more embodiments described herein. Aspects of systems (e.g., system 100 and the like), apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. Repetitive description of like elements employed in one or more embodiments described herein is omitted for sake of brevity.

Referring to FIG. 1, the system 100 can optionally include a server device, one or more networks and one or more devices (not shown). The system 100 can also include or otherwise be associated with at least one processor 102 that executes computer executable components stored in memory 104. The system 100 can further include a system bus 106 that can couple various components including, but not limited to, a receiving component 108, a model generation component 110, an identification component 112, a ranking component 114 and a disease progression model 116. The system 100 can be any computing device or set of computing devices that can be communicatively coupled to devices, non-limiting examples of which can include, but are not limited to, a server computer, a computer, a mobile computer, a mainframe computer, an automated testing system, a network storage device, a communication device, a web server device, a network switching device, a network routing device, a gateway device, a network hub device, a network bridge device, a control system, or any other suitable computing device. A device can be any device that can communicate information with the system 100 and/or any other suitable device that can employ information provided by system 100. It is to be appreciated that system 100, components, models or devices can be equipped with communication components (not shown) that enable communication between the system, components, models, devices, etc. over one or more networks.

The various components (e.g., receiving component 108, model generation component 110, an identification component 112, ranking component 114, disease progression model 116, and/or other components) of system 100 can be connected either directly or via one or more networks. Such networks can include wired and wireless networks, including, but not limited to, a cellular network, a wide area network (WAN) (e.g., the Internet), or a local area network (LAN), non-limiting examples of which include cellular, WAN, wireless fidelity (Wi-Fi), Wi-Max, WLAN, radio communication, microwave communication, satellite communication, optical communication, sonic communication, or any other suitable communication technology.

The receiving component 108 receives and learns observational patient data. Observational databases such as disease registry data and Electronic Health Records (EHR) contain longitudinal information about patients, which are instrumental for tracking progression of chronic diseases. However, tracking disease progression may not be a primary goal when observational data are collected. Therefore, tracking disease progression directly based on 'raw' observational datasets can be difficult. Multiple clinical assessments are collected in observational data for multiple purposes, and not all assessments may be relevant for purpose of tracking disease progression. Among assessments targeting for monitoring disease progression, not all have same sensitivity or efficiency to discriminate patients at different disease stages. An assessment may not have the same discriminative power across whole course of a target disease. For example, chorea symptom is most prominent in early to middle stages of Huntington's Disease (HD). An assessment for measuring the chorea symptom may not be as efficient for late stage HD patients. Disease stages may not have clear and well accepted definition, especially for complex diseases and rare diseases, which makes the problem more complicated. Electronic Health Record (EHS) as available in current form is not designed to track disease progression. EHS tracks by patients based on diagnosis, medication, lab results and other patient data such as for example: body mass index and aspects. There is no indication from the EHS which features can be useful and how efficient they are for tracking disease progression. Enroll-HD is an example of Disease Registry Data (DRD) (see e.g., FIG. 5). DRD is more targeted for individual diseases, the features collected could be used to evaluate social, economic as well as health impact of the disease on patients. DRD is currently available for multiple diseases and can be used as a basis to seed the disease progression model described herein. Not all features can be efficient and sensitive for tracking disease progression plus currently there is no association or discriminative power of relevant features for tracking of disease progression at different disease states. Disease states are also not clearly labelled in the disease registry data.

The subject system 100 overcomes many of the deficiencies associated with the state of the art. The system 100 performs a secondary use of collected observational data by tracking disease progression from what can be gleaned from the observational data. To track disease progression the system can analyze, determine or infer certain clinical assessments that could be useful to distinguish types of stages along a disease progression pathway. The system 100 generates and utilizes the disease progression model 116 that transforms the original observational data into set(s) of new data, e g, making up respective data bases that rank collected clinical features by respective discriminative power to distinguish different disease stages. One of the sets of data is a reduced database of the original superset of observational data; this new reduced set of observational data converges on clinical features that have power to track different disease stages along a disease progression pathway. Thus, a more targeted database is generated, as compared to the original larger database of observational data. This more targeted database has features with high power to distinguish different stages of disease progression along a pathway.

The model generation component 110 builds a preliminary disease progression model based on the observational data from the receiving component 108. The identification component 112 identifies discriminative clinical features for different disease stages. The ranking component ranks discriminative powers of clinical features for respective pairs of disease stages; wherein the model generation component 110 employs the ranked features to generate the final disease progression model 116.

Figure 2:
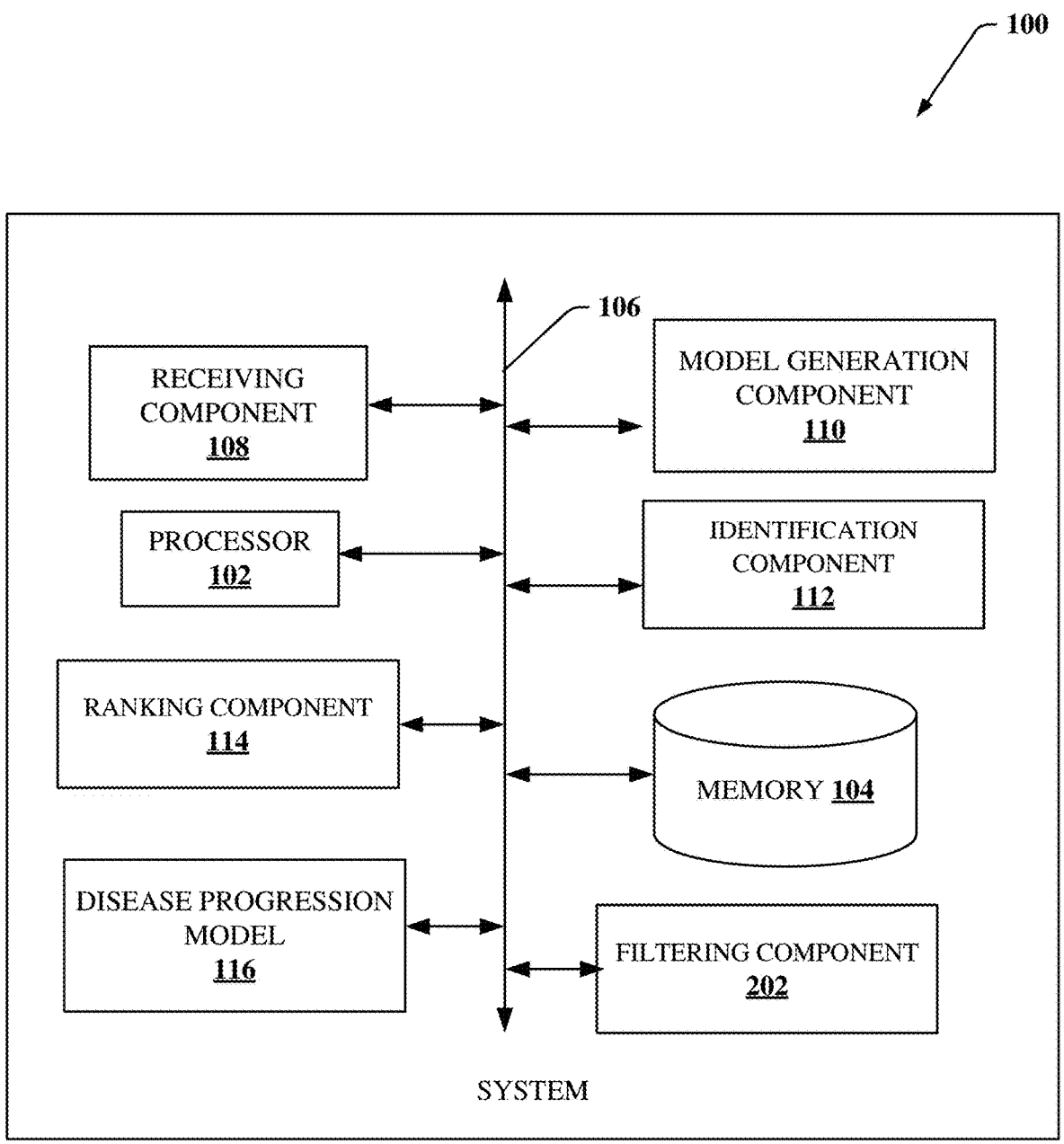
FIG. 2 illustrates a block diagram of an example system that provides for generation and employment of disease progression model(s) that facilitate identifying and indexing discriminative features for disease progression in observational data in accordance with one or more implementations described herein.

FIG. 2 illustrates an embodiment of the system 100 that includes a filter component 202. The filtering component 202 combines existing medical knowledge of a target disease as well as availability of clinical features in the observational patient data to perform an initial feature filtering. The filtering component filters features most irrelevant to disease progression to generate a reduced dataset.

Figure 3:
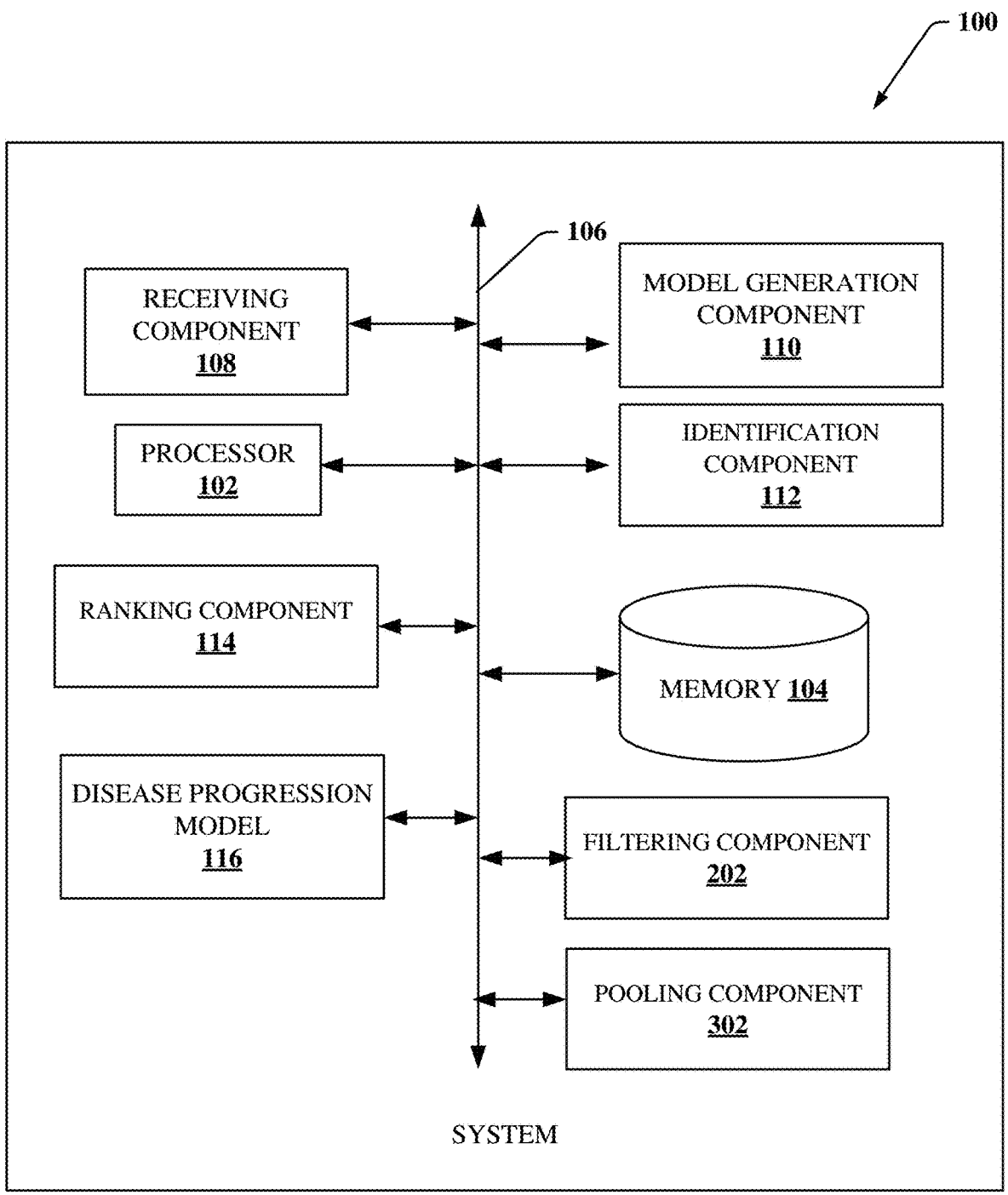
FIG. 3 illustrates a block diagram of an example system that provides for generation and employment of disease progression model(s) that facilitate identifying and indexing discriminative features for disease progression in observational data in accordance with one or more implementations described herein.

FIG. 3 illustrates an embodiment of system 100 that includes a pooling component 302 that for respective pairs of disease stages, pools clinical features and the ranking component ranks clinical features by their effective sizes.

In an embodiment of the system 100, the identification component 112 can perform a composite feature engineering step to identify underlying disease progression directions from the reduced dataset. The final disease progression model 116 can be built based on composite features for data-driven disease stage segmentation, and assignment of respective observations to a disease stage. For respective clinical features in the original observational patent data, assigned disease stages are used as benchmarks to obtain effective sizes of clinical features for respective pairs of disease stages. The final disease progression model contains clinical features effective for discriminating respective pairs of disease stages.

It is to be appreciated that in an embodiment, the final disease progression model 116 can employ a utility-based analysis to factor the benefit of making a correct prediction against the cost of making an incorrect correct prediction.

While FIGS. 1-3 depict separate components in system 100, it is to be appreciated that two or more components can be implemented in a common component. Further, it is to be appreciated that the design of the system 100 can include other component selections, component placements, etc., to facilitate automatically determining clinical features effective for discriminating respective disease stages in a particular context in accordance with one or more embodiments described herein. Moreover, the aforementioned systems and/or devices have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components can be combined into a single component providing aggregate functionality. The components can also interact with one or more other components not specifically described herein for the sake of brevity, but known by those of skill in the art.

Further, some of the processes performed can be performed by specialized computers for carrying out defined tasks related to automatically determining clinical features effective for discriminating respective disease stages in a particular context. The subject computer processing systems, methods apparatuses and/or computer program products can be employed to solve new problems that arise through advancements in technology, computer networks, the Internet and the like. The subject computer processing systems, methods apparatuses and/or computer program products can provide technical improvements to systems automatically determining clinical features effective for discriminating respective disease stages in a particular context in a live environment by improving processing efficiency among processing components in these systems, reducing delay in processing performed by the processing components, and/or improving the accuracy in which the processing systems automatically determine privacy for a user and a product in a particular context.

The embodiments of devices described herein can employ artificial intelligence (AI) to facilitate automating one or more features described herein. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) described herein, components described herein can examine the entirety or a subset of the data to which it is granted access and can provide for reasoning about or determine states of the system, environment, etc. from a set of observations as captured via events and/or data. Determinations can be employed to identify a specific context or action, or can generate a probability distribution over states, for example. The determinations can be probabilistic—that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, etc.)) schemes and/or systems (e.g., support vector machines, neural networks, expert systems, Bayesian belief networks, fuzzy logic, data fusion engines, etc.) in connection with performing automatic and/or determined action in connection with the claimed subject matter. Thus, classification schemes and/or systems can be used to automatically learn and perform a number of functions, actions, and/or determination.

A classifier can map an input attribute vector, z=(z1, z2, z3, z4, ..., zn), to a confidence that the input belongs to a class, as by f(z)=confidence(class). Such classification can employ a probabilistic and/or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and/or probabilistic classification models providing different patterns of independence can be employed. Classification as used herein also is inclusive of statistical regression that is utilized to develop models of priority.

Figure 4:
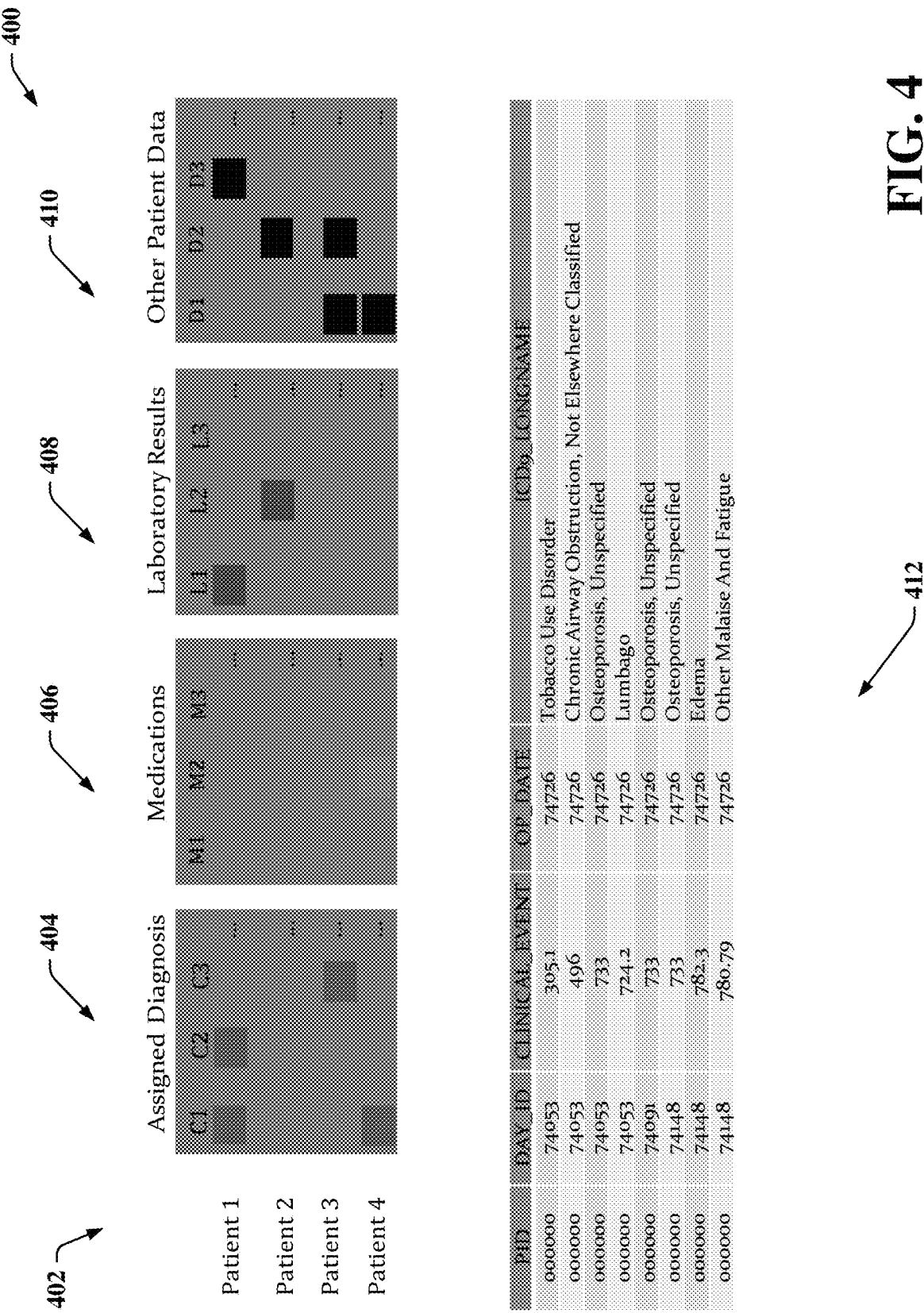
FIG. 4 illustrates a block diagram of an example, Electronic Health Record as currently defined which identifies Assigned Diagnosis, Medication, Lab Results and Other Data for respective patient data in accordance with one or more implementations described herein.
Figure 5:
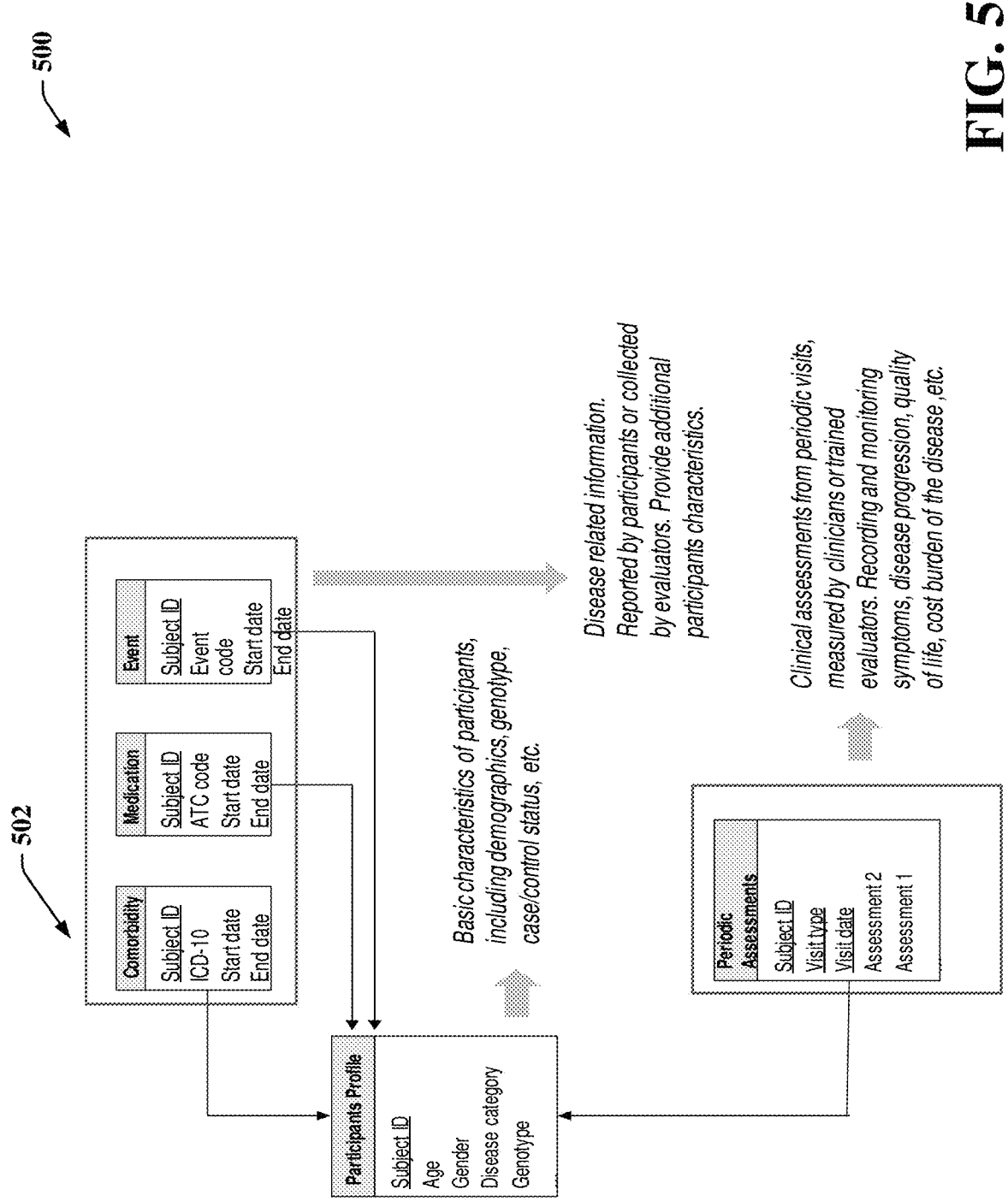
FIG. 5 illustrates a schematic diagram an example of disease registry data that can be used to track disease progression data in accordance with one or more implementations described herein.

FIGS. 4 and 5 illustrate non-limiting real-world examples of observational data. Embodiments described herein can be applied to such types of observational data as well as multitudes of other suitable types of observational data. FIG. 4 illustrates an electronic health record set of data 400 with a structure as shown. FIG. 5 illustrates an example set of disease registry data 500. In FIG. 4, a set of patients (e.g., patient 1-patient 4) 402 are depicted—it is to be appreciated that any suitable number (N) of patients can be represented by this data set. A set of assigned diagnoses 404 (e.g., C1-C3) are shown. C1 could represent Type I diabetes, C2 could represent coughing, while C3 could represent bronchitis for example. A set of data resenting medications 406 corresponding to the respective patient and diagnosis is shown. Laboratory results 408 (e.g., L1-L3) and other patient data (e.g., D1-D3) are illustrated. For example, the other patient data could include age, body-mass-index (BMI). Dataset 412 includes patient identification (PID), day/time an event occurred (Day_ID), clinical event (CLINICAL_EVENT), Operation Date (OP_Date), and detailed explanation of IC code (ICD$_9$_LONGNAME). Such conventional EHR dataset 400 is not designed for tracking disease progression; heterogeneous types of information are collected. Some features, e.g. lab test results and medication records, could be useful for tracking the progression of a target disease. The dataset 400 as originally constructed was not intended nor provides indication about which features could be useful, and how efficient they are for tracking disease progression. However, for example, some of the clinical events could be useful in connection with tracking disease progression along a particular disease pathway, while other clinical events not useful.

FIG. 5 illustrates an example of enrolling health data as an example disease registry data. Disease registry data is typically targeted for a particular disease. However, the features collected in disease registry data may have particular uses. For example, some of the features collected may be evaluated to gauge socio-economic impact of the particular disease on patient(s). Each of the respective tables 502 (e.g., Event, Medication, Comorbidity, Participants Profile, Periodic Assessments) of the disease registry data 500 can provide different types of information. Tracking disease progression could be one of multiple targets of disease registry data. Not all features can be efficient and sensitive for tracking disease progression. No information is available in conventional disease registry data to readily identify relevant features. There is no evaluation about the discriminative power of relevant features for tracking disease progression at different disease states; and disease states may not be clearly labelled in disease registry data. In accordance with embodiments described herein, the disease registry data 500 can be learned by the disease progression model 116 to generate a more refined database that is useful for tracking disease progression.

Electronic Health Record (EHS) is not designed to track disease progression. EHS tracks by patients based on diagnosis, medication, lab results and other patient data like body mass index, age and others. There is no indication which features could be useful and how efficient they are for tracking disease progression. Enroll-HD is an example of Disease Registry Data (DRD) is more targeted for individual disease, the features collected could be used to evaluate social, economic as well as health impact of the disease on patients. DRD is currently available for multiple diseases and is used as a basis to seed the disease progression model. Not all features can be efficient and sensitive for tracking disease progression plus currently there is no association or discriminative power of relevant features for tracking of disease progression at different disease states. Disease states are also not clearly labelled in the disease registry data.

Figure 6:
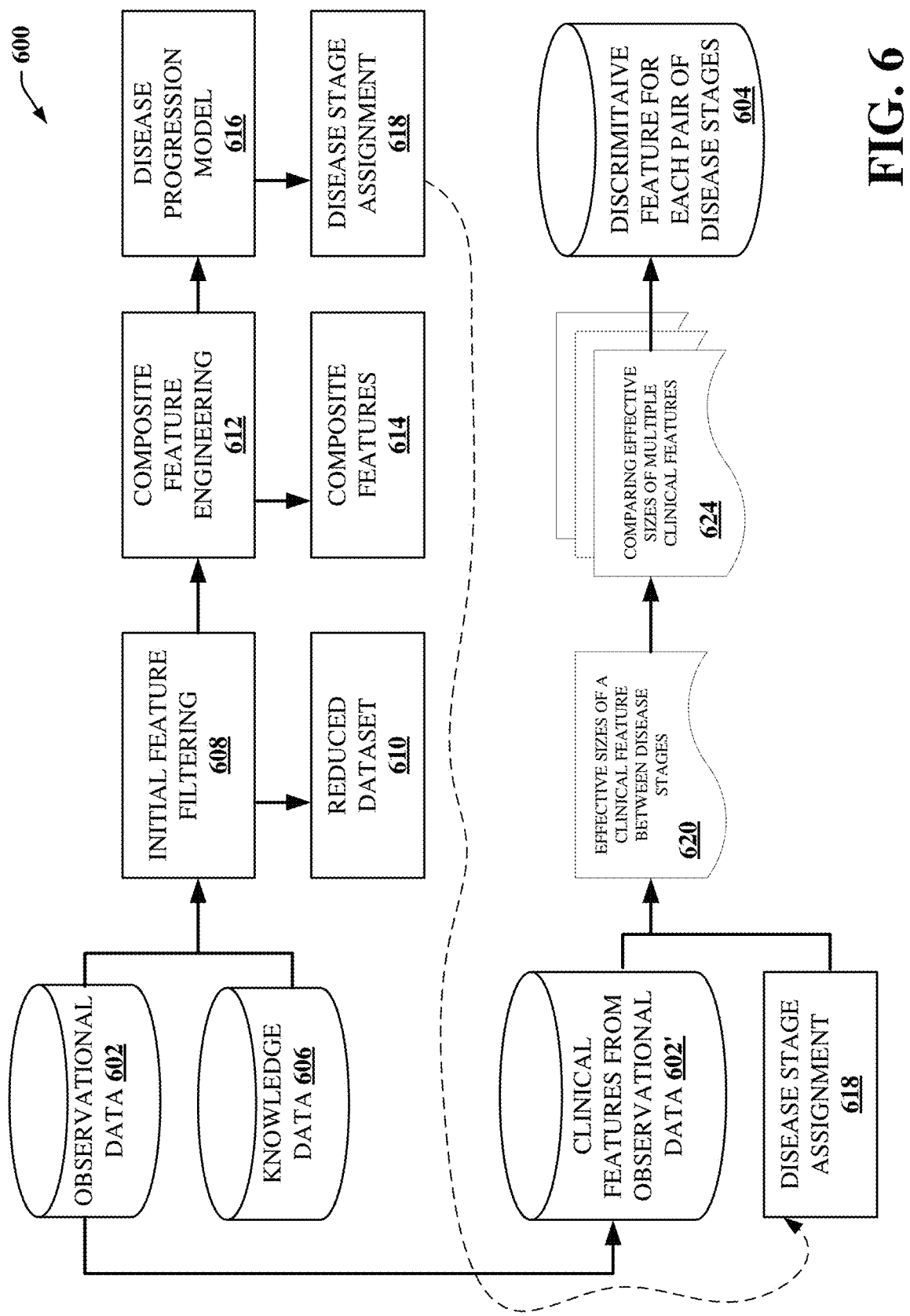
FIG. 6 illustrates a schematic flow diagram of an example disease progression model generation in accordance with one or more implementations described herein.

FIG. 6 illustrates a schematic diagram 600 of various acts associated with generating a generate a more refined database 604 that is useful for tracking disease progression. Various Electronic Health Record(s) (EHR) or Disease Registry Data (DRD) for can be employed as bases for a set of observational data 604. A set of knowledge data 606, e.g., representing extensive knowledge of a target disease are analyzed by the disease progression model 116 (see FIGS. 1-3). These databases feed into an Initial Feature Filtering (IFF) 608 which is developed based on the disease knowledge. The IFF reduces the data for respective patients into manageable reduced datasets 610. A Composite Feature Engineering (CFE) 612 is performed, e.g., using multiple models based on different sets of data; graphical modeling can also be used to extract underlying progression patterns from features to generate composite features at 614. After CFE 612, disease progression modeling is performed at 616 the next step is Disease Progression Modeling (DPM) which can use multiple methodologies to build the model 116. For example, a semi-Markov jump process can be used to extract DPM using Health Record data. The disease progression modeling 116 results in disease stage assignment 618. A goal of this preliminary state within the disease progression modeling (DPM) is to map respective patients at respective observation to specific disease states. The preliminary model generated from stage 1 feeds into stage 2. In stage 2, the observational data is the same but refined with clinical features, e.g., time stamps for respective patients showing disease progression thereby creating longitudinal data that is specific for respective patients. This creates for respective patients a sequence of observations and data with time stamp(s) to map patient condition within a specific disease state. This patient specific data mapped along a disease pathway is what is included in a Disease Stage Assignment database (C). Respective diseases now have respective pathways created that identify and define effective sizes of clinical features at respective disease stages. Also identified are features that could have high power to distinguish where respective patients are at for given disease stages. For each clinical feature under each pair of disease stage using statistical information, key value can be attached. At 620, The key value can indicate power of the feature to distinguish between disease stage. At 624, this information is collected and compared to develop effective multiple clinical feature sizes for respective disease stages. Top features will be the most discriminative feature for each pair of disease stage. The output 604 includes discriminative features for each pair of disease stages that are important to track and form the refined disease progression model. The output 604 is also an implication from the disease progression model and is refined based on clinical features of patients as they transition through various stages of a disease.

Figure 7:
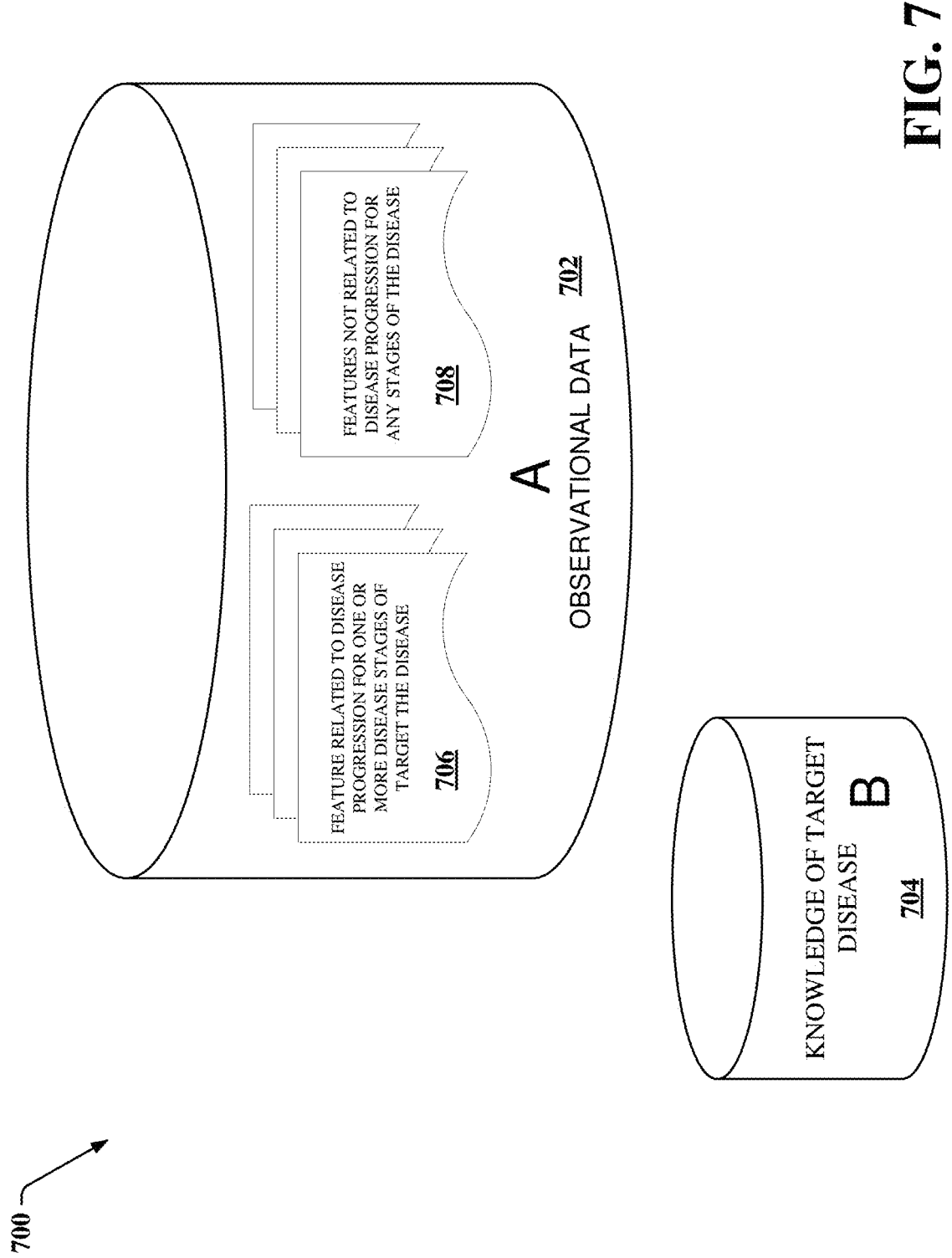
FIG. 7 illustrates a schematic diagram of example observational data base and knowledge database data in accordance with one or more implementations described herein.

FIG. 7 illustrates input data 700 divided into constituent parts: observational data (A) 702 and data based on knowledge of target diseases (B) 704. The observational data 702 is further divided based on features related to disease progression for one or more disease states 706, and features not related to disease progression for any of the disease stages 708. Data type 706 contains longitudinal information that is patient specific but there is no discriminative power of features for distinguishing patients at different stages. Knowledge of target disease database B 704 is not structured and is available in many literature and may contain, for example: (1) one or a few widely used biomarkers; (2) definition or description of disease stages/states; or (3) information on respective treatment(s) that could slow down or reverse disease progression. Both types of data 706 and 708 may available in various data formats and can use machine learning system to pull in data from various outside sources.

Figure 8:
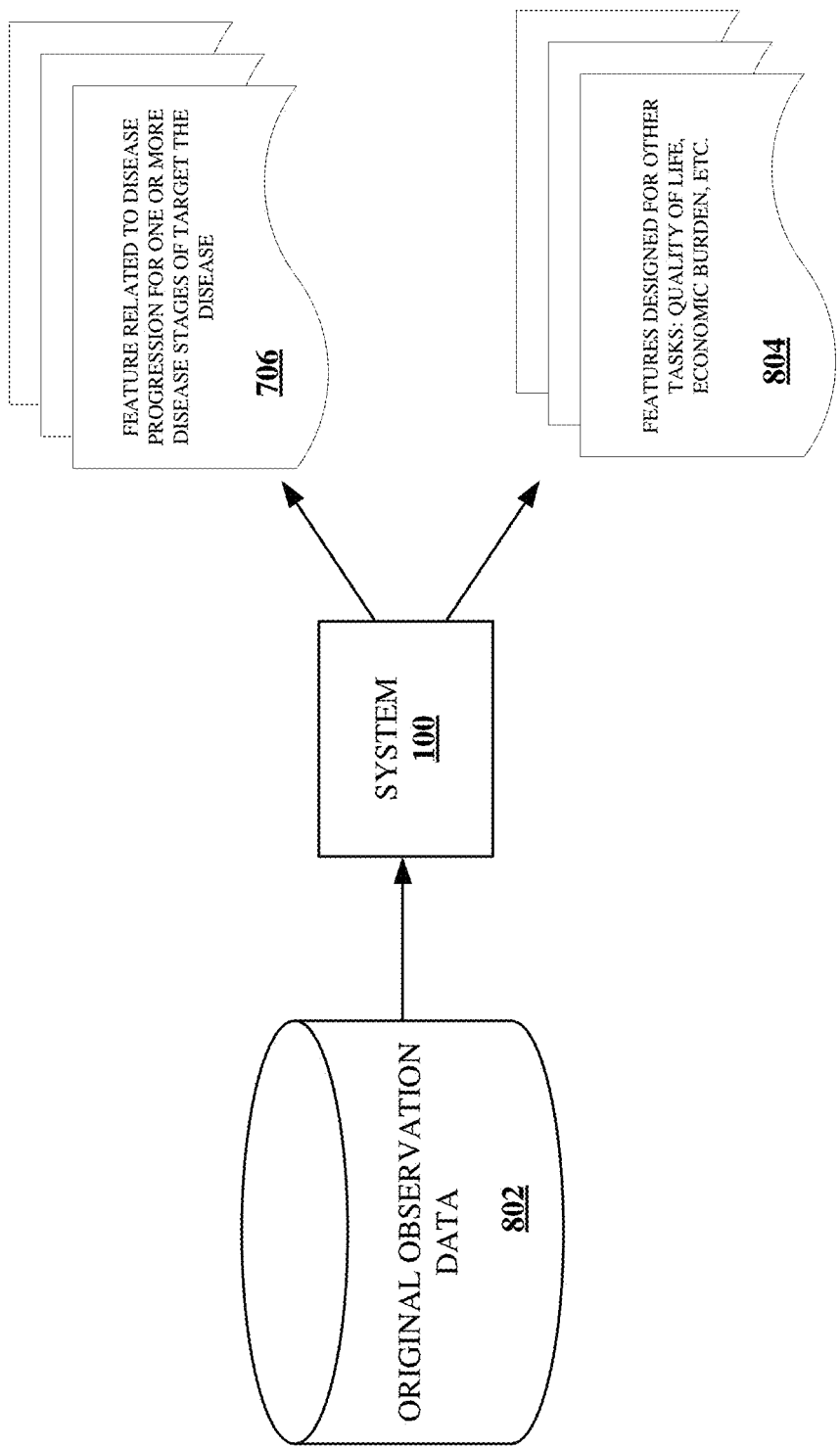
FIG. 8 illustrates a schematic diagram of original observation data being analyzed and by a system and relevant features extracted therefrom data in accordance with one or more implementations described herein.

FIG. 8 schematically illustrates original observation data 802 being analyzed by system 100 (See e.g., FIGS. 1-3) where the system 100 extracts features related to disease progression for one or more disease stages of the target disease 706, and extracts features designed for other tasks such as for example: quality of life, economic burden, etc.

Figure 9:
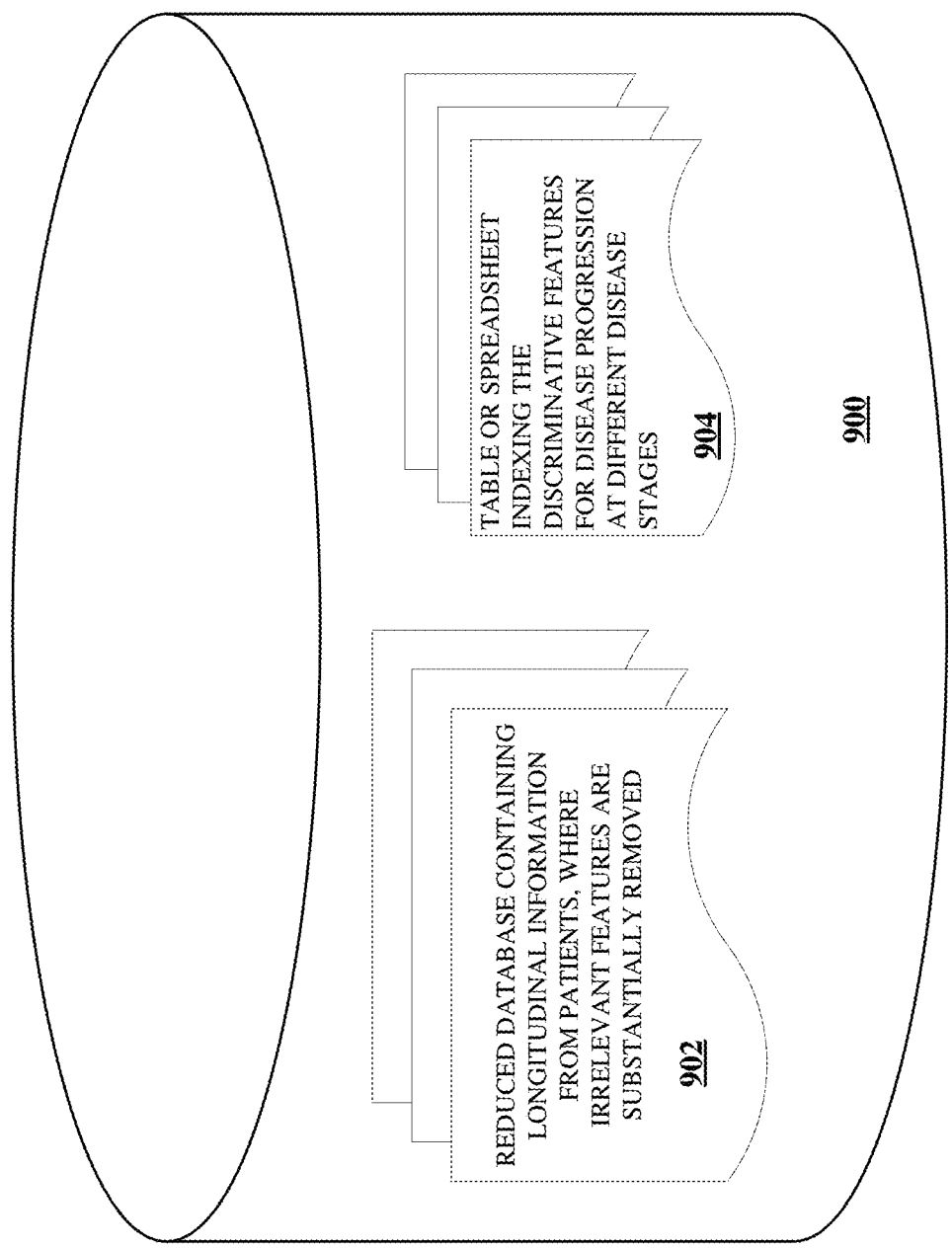
FIG. 9 illustrates a schematic representation of a reduced database in accordance with one or more implementations described herein.

FIG. 9 is a description of an output database 900 generated by system 100 (FIG. 1) based on original observational data. The final database 900 comprises a reduced database 1102 containing longitudinal information from patients, where irrelevant features are substantially removed, and can also attach discriminative features 1104 that are relevant to disease progression. These features in sub-database 1002 may only be effective in a subset of the disease stages/states. The discriminative features sub-database 1004 can take respective features indicated in sub-database 1002 and determine how relevant they are during respective disease stages and how much discriminating power they have at respective disease stages. The discriminative powers and features can be easily extracted and used for tracking of disease progression at different stages/states. The final database 1000 can include a table or spreadsheet 1104 indexing the discriminative features for disease progression (e.g., as shown below in Table 1).

TABLE 1

| FEATURE NAME | DISEASE STAGE E | DISEASE STAGE F | DISCRIMINATIVE POWER |
|---|---|---|---|
| Feature 1 | 1 | 2 | 1.1 |
| Feature 1 | 2 | 3 | 0.9 |
| Feature 2 | 1 | 2 | 0.77 |
| . . . | . . . | . . . | . . . |

Figure 10:
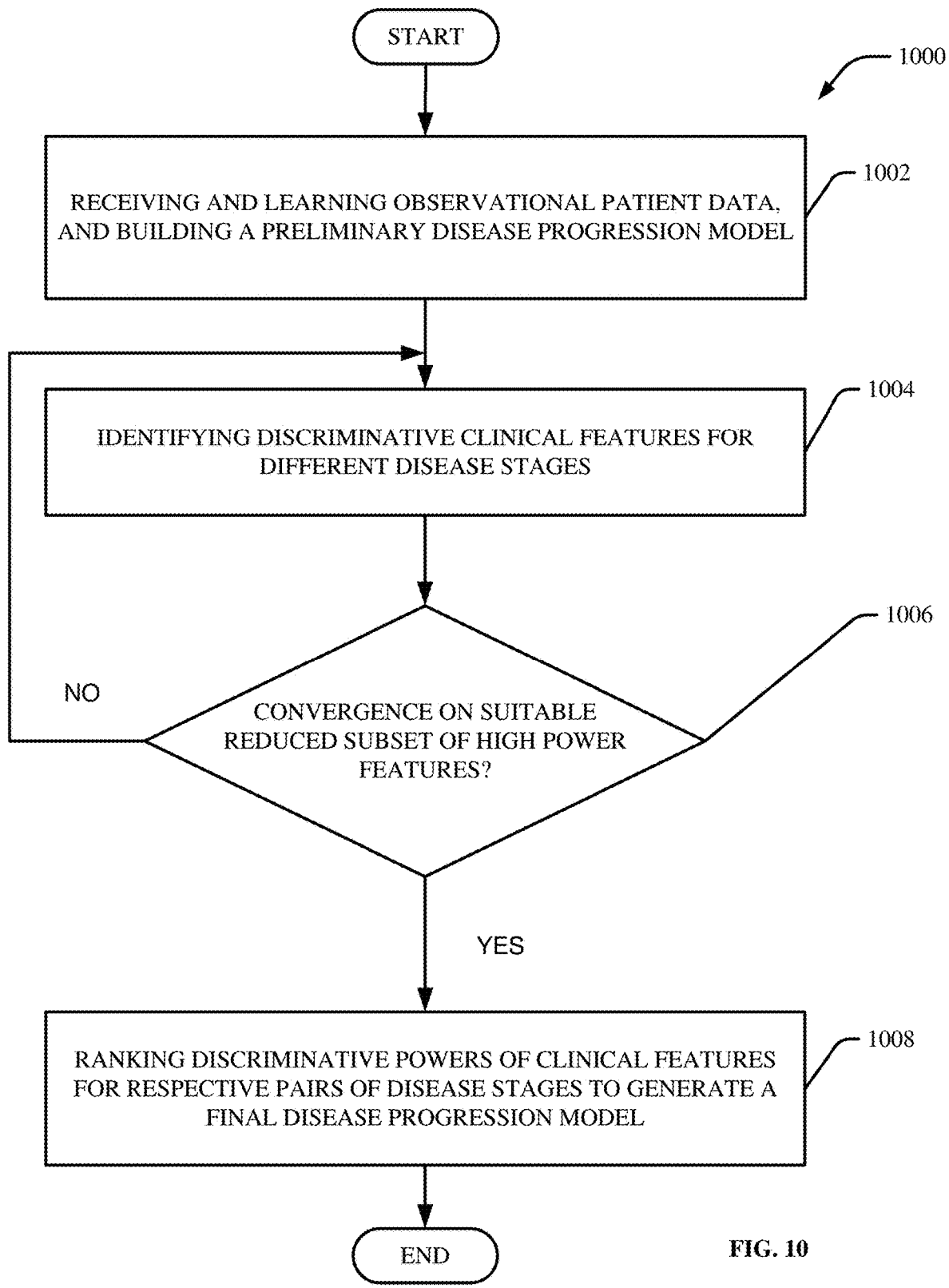
FIG. 10 is a flow diagram relating to generation and employment of disease progression model(s) that facilitate identifying and indexing discriminative features for disease progression in observational data in accordance with one or more implementations described herein.

FIG. 10 illustrates a flow diagram of an example, non-limiting computer-implemented method 1000 that overcomes many of the deficiencies associated with the state of the art. The method 1000 performs a secondary use of collected observational data by tracking disease progression from what can be gleaned from the observational data. To track disease progression the method can analyze, determine or infer certain clinical assessments that could be useful to distinguish types of stages along a disease progression pathway. The method 1000 generates and utilizes the disease progression model 116 (FIG. 1) that transforms an original observational data into set(s) of new data, e g, making up respective data bases that ranks collected clinical features by respective discriminative power to distinguish different disease stages. One of the sets of data is a reduced database of the original superset of observational data; this new reduced set of observational data converges on clinical features that have power to track different disease stages along a disease progression pathway. Thus, a more targeted database is generated, as compared to the original larger database of observational data. This more targeted database has features with high power to distinguish different stages of disease progression along a pathway.

At 1002, the method builds a preliminary disease progression model (e.g., using the model generation component 110) based on received observational data (e.g., received by the receiving component 108). At 1004, the method identifies discriminative clinical features for different disease stages (e.g., using the identification component 112). At 1006, a determination is made as to whether convergence on a suitable reduced subset of high power features has been obtained (e.g., using the model generation component 116). At 1008, the method ranks discriminative powers of clinical features for respective pairs of disease stages (e.g., using the ranking component 114); and wherein the model generation component 110 employs the ranked features to generate the final disease progression model 116.

For simplicity of explanation, the computer-implemented methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts can be required to implement the computer-implemented methodologies in accordance with the disclosed subject matter. In addition, those skilled in the art will understand and appreciate that the computer-implemented methodologies could alternatively be represented as a series of interrelated states via a state diagram or events. Additionally, it should be further appreciated that the computer-implemented methodologies disclosed hereinafter and throughout this specification are capable of being stored on an article of manufacture to facilitate transporting and transferring such computer-implemented methodologies to computers. The term article of manufacture, as used herein, is intended to encompass a computer program accessible from any computer-readable device or storage media.

Figure 11:
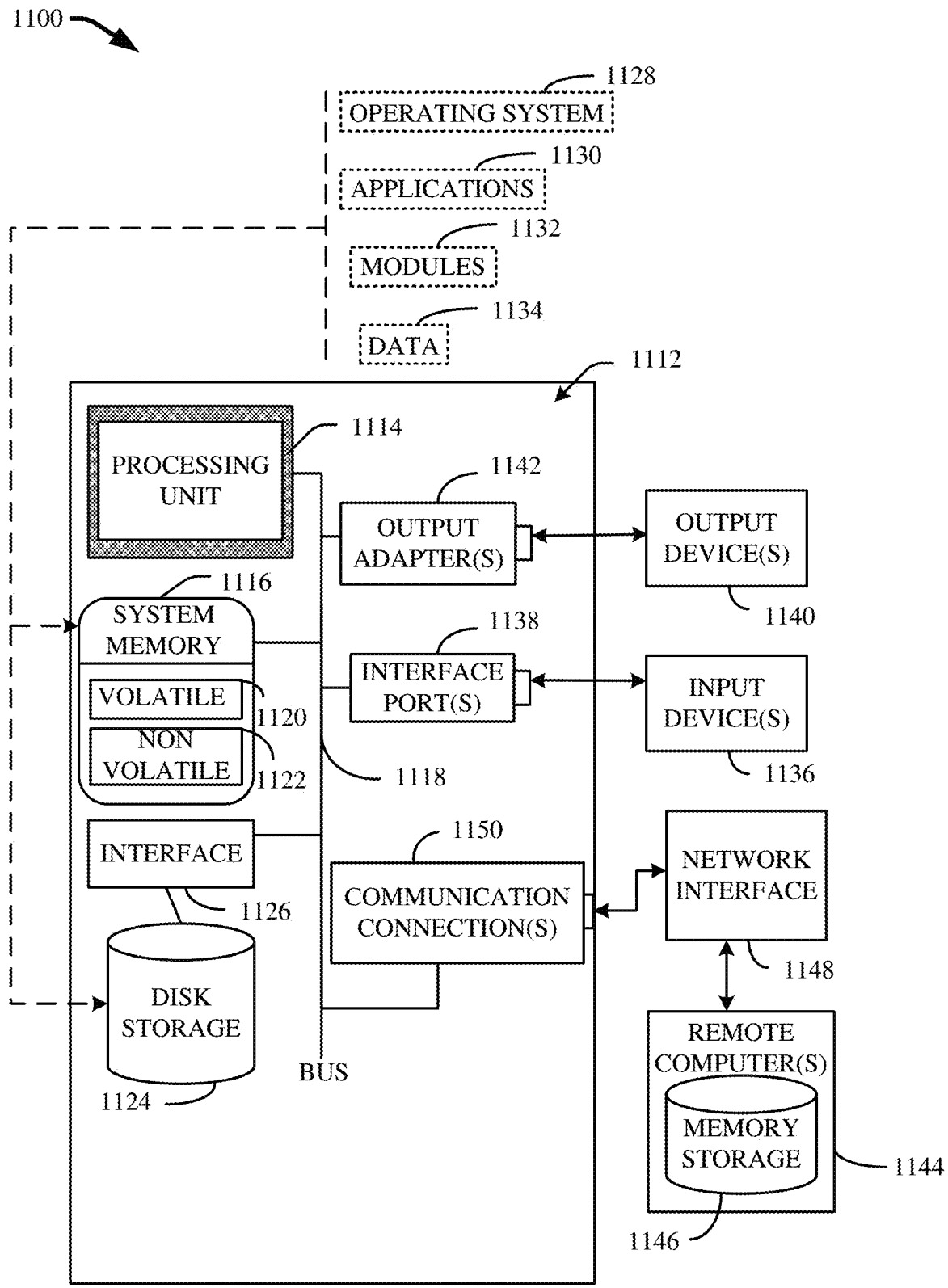
FIG. 11 is a schematic diagram of an example operating environment in accordance with one or more implementations described herein.

In order to provide a context for the various aspects of the disclosed subject matter, FIG. 11 as well as the following discussion are intended to provide a general description of a suitable environment in which the various aspects of the disclosed subject matter can be implemented. FIG. 11 illustrates a block diagram of an example, non-limiting operating environment in which one or more embodiments described herein can be facilitated. Repetitive description of like elements employed in other embodiments described herein is omitted for sake of brevity.

With reference to FIG. 11, a suitable operating environment 1100 for implementing various aspects of this disclosure can also include a computer 1112. The computer 1112 can also include a processing unit 1114, a system memory 1116, and a system bus 1118. The system bus 1118 couples system components including, but not limited to, the system memory 1116 to the processing unit 1114. The processing unit 1114 can be any of various available processors. Dual microprocessors and other multiprocessor architectures also can be employed as the processing unit 1114. The system bus 1118 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1094), and Small Computer Systems Interface (SCSI). The system memory 1116 can also include volatile memory 1120 and nonvolatile memory 1122. The basic input/output system (BIOS), containing the basic routines to transfer information between elements within the computer 1112, such as during start-up, is stored in nonvolatile memory 1122. By way of illustration, and not limitation, nonvolatile memory 1122 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1120 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1112 can also include removable/non-removable, volatile/non-volatile computer storage media. FIG. 11 illustrates, for example, a disk storage 1124. Disk storage 1124 can also include, but is not limited to, devices like a magnetic disk drive, floppy disk drive, tape drive, Jaz drive, Zip drive, LS-100 drive, flash memory card, or memory stick. The disk storage 1124 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1124 to the system bus 1118, a removable or non-removable interface is typically used, such as interface 1126. FIG. 11 also depicts software that acts as an intermediary between users and the basic computer resources described in the suitable operating environment 1101. Such software can also include, for example, an operating system 1128. Operating system 1128, which can be stored on disk storage 1124, acts to control and allocate resources of the computer 1112. System applications 1130 take advantage of the management of resources by operating system 1128 through program modules 1132 and program data 1134, e.g., stored either in system memory 1116 or on disk storage 1124. It is to be appreciated that this disclosure can be implemented with various operating systems or combinations of operating systems. A user enters commands or information into the computer 1112 through input device(s) 1136. Input devices 1136 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1114 through the system bus 1118 via interface port(s) 1138. Interface port(s) 1138 include, for example, a serial port, a parallel port, a game port, and a universal serial bus (USB). Output device(s) 1140 use some of the same type of ports as input device(s) 1136. Thus, for example, a USB port can be used to provide input to computer 1112, and to output information from computer 1112 to an output device 1140. Output adapter 1142 is provided to illustrate that there are some output devices 1140 like monitors, speakers, and printers, among other output devices 1140, which require special adapters. The output adapters 1142 include, by way of illustration and not limitation, video and sound cards that provide a means of connection between the output device 1140 and the system bus 1118. It should be noted that other devices and/or systems of devices provide both input and output capabilities such as remote computer(s) 1144.

Computer 1112 can operate in a networked environment using logical connections to one or more remote computers, such as remote computer(s) 1144. The remote computer(s) 1144 can be a computer, a server, a router, a network PC, a workstation, a microprocessor based appliance, a peer device or other common network node and the like, and typically can also include many or all of the elements described relative to computer 1112. For purposes of brevity, only a memory storage device 1146 is illustrated with remote computer(s) 1144. Remote computer(s) 1144 is logically connected to computer 1112 through a network interface 1148 and then physically connected via communication connection 1150. Network interface 1148 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1150 refers to the hardware/software employed to connect the network interface 1148 to the system bus 1118. While communication connection 1150 is shown for illustrative clarity inside computer 1112, it can also be external to computer 1112. The hardware/software for connection to the network interface 1148 can also include, for exemplary purposes only, internal and external technologies such as, modems including regular telephone grade modems, cable modems and DSL modems, ISDN adapters, and Ethernet cards.

Embodiments of the present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a server computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems, computer program products, and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising: a memory that stores computer executable components; a processor, operably coupled to the memory, that executes computer executable components stored in the memory, wherein the computer executable components comprise: a receiving component that receives and learns observational patient data; a model generation component that builds a preliminary disease progression model based on the observational patient data received from the receiving component; an identification component that automatically identifies discriminative clinical features for different disease stages in a particular context in a live environment; and a ranking component that ranks discriminative powers of the clinical features for respective pairs of disease stages; wherein the model generation component also employs ranked clinical features from the ranking component to generate a final disease progression model that employs a utility-based analysis to factor benefit of making a correct prediction against cost of making an incorrect prediction, wherein generation of the final disease progression model, by the model generation component, comprises: determination of component features for data-driven disease stage segmentation; assignment of respective observations to one of the disease stages employing a semi-Markov jump process to generate disease progression modeling resulting in disease stage assignment; for respective ones of the clinical features in the observational patient data, employing assigned disease stages as benchmarks to obtain effective sizes of the clinical features for the respective pairs of disease stages, wherein the clinical features are time stamps for respective patients showing disease progression thereby creating longitudinal data that is specific for respective patients, and wherein the final disease progression models contain ones of the clinical features effective for the discriminating respective pairs of disease stages.

2. The system of claim 1, wherein the computer executable components further comprise a filtering component that combines existing medical knowledge of a target disease as well as availability of clinical features in the observational patient data to perform an initial feature filtering.

3. The system of claim 2, wherein the filter component filters features most irrelevant to disease progression to generate a reduced dataset.

4. The system of claim 3, wherein the identification component performs composite feature engineering to identify underlying disease progression directions from the reduced dataset.

5. The system of claim 1, wherein the computer executable components further comprise a pooling component that, for respective pairs of disease stages, pools clinical features and the ranking component ranks the clinical features by respective effective size.

6. The system of claim 1, wherein the final disease progression model contains clinical features effective for discriminating respective pairs of disease stages, and wherein the system further comprises displaying a table or a spreadsheet indexing the discriminative clinical features for disease progression.

7. A computer-implemented method, comprising:
receiving and learning, by a system operatively coupled to a processor, observational patient data, and building a preliminary disease progression model;
automatically identifying, by the system, discriminative clinical features for different disease stages;
ranking, by the system, discriminative powers of clinical features for respective pairs of disease stages; and
generating, by the system, a final disease progression model, wherein the generating comprises:
assigning respective observations to one of the disease stages employing a semi-Markov jump process to generate disease progression modeling resulting in disease stage assignment;
determining effective sizes of the clinical features for the respective pairs of disease stages based on comparing key values attached to the clinical features, wherein the key values are indicative of abilities of respective ones of the clinical features to distinguish between the disease stages; and
for respective ones of the clinical features in the observational patient data, employing assigned disease stages to obtain effective sizes of the clinical features for the respective pairs of disease stages.

8. The computer-implemented method of claim 7, further comprising combining existing medical knowledge of a target disease as well as availability of clinical features in the observational patient data to perform an initial feature filtering, and wherein the disease stage assignment is an assignment of a numerical value.

9. The computer-implemented method of claim 8, further comprising filtering features most irrelevant to disease progression to generate a reduced dataset.

10. The computer-implemented method of claim 9, further comprising performing a composite feature engineering step to identify underlying disease progression directions from the reduced dataset.

11. The computer-implemented method of claim 10, wherein the final disease progression model is built based as a function of composite features for data-driven disease stage segmentation, and assignment of respective observations to a disease stage.

12. The computer-implemented method of claim 7, further comprising for respective pairs of disease stages, clinical features are pooled and the clinical features are ranked by effective size.

13. The computer-implemented method of claim 7, further comprising training the final disease progression model using recursive machine learning.

14. The computer-implemented method of claim 7, further comprising applying a utility-based analysis to factor benefit of making a correct prediction against cost of making an incorrect prediction.

15. A computer program product for monitoring disease progression, the computer program product comprising a computer readable storage medium having program instructions embodied therewith, the program instructions executable by a processor to cause the processor to:
    receive and learn observational patient data, and build a preliminary disease progression model;
    automatically identify discriminative clinical features for different disease stages; and
    rank discriminative powers of clinical features for respective pairs of disease stages to generate a final disease progression model that employs a utility-based analysis to factor benefit of making a correct prediction against cost of making an incorrect prediction; and
    generate a final disease progression model, wherein the generation comprises:
        assignment of respective observations to one of the disease stages employing a semi-Markov jump process to generate disease progression modeling resulting in disease stage assignment;
        selection of key values to associate with respective clinical features, wherein the key values are indicative of powers of the respective clinical features to distinguish between the disease stages; and
        determination of effective sizes of the clinical features for the respective pairs of disease stages based on comparing the key values associated with the clinical features.

16. The system of claim 1, wherein the system infers specific clinical assessments to distinguish types of the clinical stages along a disease progression pathway.

17. The system of claim 1, wherein the model generation component also attaching a key value to a respective one of the clinical features under each pair of the disease stages, wherein the key value indicates power of the respective one of the clinical features to distinguish between the disease stages.

18. The system of claim 1, effective sizes of the clinical features for the respective pairs of disease stages is obtained based on collecting and comparing respective key values indicating power of the clinical features to distinguish between the disease stages.

* * * * *